US012029583B2

(12) United States Patent
Shelly et al.

(10) Patent No.: US 12,029,583 B2
(45) Date of Patent: Jul. 9, 2024

(54) SYSTEM AND METHOD FOR PROVIDING SLEEP POSITIONAL THERAPY AND PACED BREATHING

(71) Applicant: KONINKLIJKE PHILIPS N.V., Eindhoven (NL)

(72) Inventors: Benjamin Irwin Shelly, Pittsburgh, PA (US); Monica H Bush, Murrysville, PA (US); Andreas Ralph Maihoefer, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 675 days.

(21) Appl. No.: 16/720,048

(22) Filed: Dec. 19, 2019

(65) Prior Publication Data

US 2020/0202120 A1 Jun. 25, 2020

Related U.S. Application Data

(60) Provisional application No. 62/782,409, filed on Dec. 20, 2018.

(51) Int. Cl.
*A61B 5/00* (2006.01)
*A61M 21/02* (2006.01)
(Continued)

(52) U.S. Cl.
CPC ............ *A61B 5/486* (2013.01); *A61B 5/4561* (2013.01); *A61B 5/4806* (2013.01);
(Continued)

(58) Field of Classification Search
CPC ..... A61B 5/486; A61B 5/4561; A61B 5/4806; A61B 5/4818; A61B 5/6831; A61B 5/72;
(Continued)

(56) References Cited

U.S. PATENT DOCUMENTS 4,617,525 A 10/1986 Lloyd
2011/0046434 A1 2/2011 Schmeink
(Continued)

FOREIGN PATENT DOCUMENTS

CN 103347438 A 10/2013

OTHER PUBLICATIONS

International Search Report and Written Opinion Dated Apr. 8, 2020 for International Application No. PCT/EP2019/086217 Filed Dec. 19, 2019.
(Continued)

*Primary Examiner* — James J Yang

(57) ABSTRACT

The present disclosure pertains to a system and method for providing sleep positional therapy and paced breathing to a user for a sleep session. The system and method may be used to treat positional obstructive sleep apnea, positional snoring, and/or other conditions to improve sleep onset latency, relaxation, reduce blood pressure, and/or improve other physiological characteristics. The system includes a posture sensor, a sensory stimulator, a controller, and/or other components. The system is configured to generate information related to a posture of the user, determine whether the posture of the user has breached a posture threshold, provide vibrations to the user to prompt the user to change posture, and lead the user through a paced breathing exercise to help the user fall asleep.

13 Claims, 3 Drawing Sheets

(51) Int. Cl.
    *A61B 5/11*         (2006.01)
    *A61F 5/56*         (2006.01)
    *A61M 21/00*      (2006.01)

(52) U.S. Cl.
    CPC .......... *A61B 5/4818* (2013.01); *A61B 5/6831* (2013.01); *A61B 5/72* (2013.01); *A61B 5/7455* (2013.01); *A61M 21/02* (2013.01); *A61B 5/1116* (2013.01); *A61F 5/56* (2013.01); *A61M 2021/0088* (2013.01)

(58) Field of Classification Search
    CPC ..... A61B 5/7455; A61B 5/1116; A61B 5/746; A61B 5/4836; A61B 5/1036; A61M 21/02; A61M 2021/0088; A61F 5/56
    See application file for complete search history.

(56) References Cited

U.S. PATENT DOCUMENTS

| | | |
|---|---|---|
| 2013/0043999 A1 | 2/2013 | Van Beest |
| 2013/0310636 A1 | 11/2013 | Krans |
| 2015/0364058 A1* | 12/2015 | Lagree ............... G09B 19/0038 |
| | | 434/257 |
| 2018/0192920 A1* | 7/2018 | Rosenblood ........... A61B 5/486 |
| 2020/0383580 A1* | 12/2020 | Shouldice .......... A61B 5/02416 |

OTHER PUBLICATIONS

"The Sleep Position Trainer", Night Balance, Accessed Dec. 16, 2019, https://www.nightbalance.com/spt/.

* cited by examiner

SYSTEM AND METHOD FOR PROVIDING SLEEP POSITIONAL THERAPY AND PACED BREATHING

CROSS-REFERENCE TO PRIOR APPLICATIONS

This application claims the benefit of U.S. Provisional Application No. 62/782,409, filed on 20 Dec. 2018. This application is hereby incorporated by reference herein.

BACKGROUND

1. Field

The present disclosure pertains to a system and method for providing sleep positional therapy and paced breathing to a user for a sleep session.

2. Description of the Related Art

Electronic positional sleep therapy devices are known. One such device is described in U.S. Patent Application Publication Number 2013/0043999. Typical positional sleep therapy devices detect whether a user is sleeping on his or her back, and provide vibratory feedback to the user that prompts the user to change his or her position. A more traditional method of positional sleep training is known as the "Tennis Ball Technique". With this technique, a tennis ball is sewn into the back of a shirt worn to bed by the user so that the user finds sleeping on his or her back uncomfortable. Known electronic positional sleep therapy devices and the Tennis Ball Technique do not provide any other sleep assistance to a user.

SUMMARY

It would be advantageous to provide an electronic positional sleep therapy system configured to provide additional sleep assistance to a user. For example, it would be advantageous to provide an electronic positional sleep therapy system configured to assist a user in falling asleep.

Accordingly, one or more aspects of the present disclosure relate to a system configured to provide sleep positional therapy and paced breathing to a user for a sleep session. The system comprises one or more posture sensors, one or more sensory stimulators, a controller, and/or other components. The one or more posture sensors are configured to generate output signals conveying information related to a posture of the user. The one or more sensory stimulators are configured to provide sensory stimulation to the user. The controller is coupled to the one or more posture sensors and the one or more sensory stimulators. The controller is configured to determine, based on the output signals, whether the posture of the user has breached a posture threshold. Responsive to a breach, the controller is configured to cause the one or more sensory stimulators to provide first sensory stimulation to the user to prompt the user to change posture such that the posture of the user no longer breaches the posture threshold. Responsive to determining that the posture of the user no longer breaches the posture threshold, the controller is configured to cause the one or more sensory stimulators (e.g., the same sensory stimulator that provided the first sensory stimulation, or a different sensory stimulator) to provide second sensory stimulation that leads the user through a paced breathing exercise.

In some embodiments, the controller is further configured to cause the one or more sensory stimulators to provide third sensory stimulation that prompts the user to indicate whether the user is ready for the paced breathing exercise before the user is led through the paced breathing exercise.

In some embodiments, the one or more posture sensors are further configured to receive an indication from the user that the user is ready for the paced breathing exercise, and the controller is further configured to cause the one or more sensory stimulators to provide the second sensory stimulation that leads the user through the paced breathing exercise responsive to the one or more posture sensors receiving the indication that the user is ready for the paced breathing exercise.

In some embodiments, the controller is configured to cause the one or more sensory stimulators to provide the second sensory stimulation that leads the user through the paced breathing exercise before or during the sleep session responsive to receiving the indication from the user that the user is ready for the paced breathing exercise, and independent of the determination of whether the posture of the user has breached the posture threshold.

In some embodiments, the system further comprises one or more physiological sensors configured to generate output signals conveying information related to respiration of the user. In these embodiments, the controller is configured to cause delivery of the sensory stimulation during inhalation and exhalation portions of the paced breathing exercise based on the information in the output signals from the one or more physiological sensors.

In some embodiments, the controller is configured such that causing the one or more sensory stimulators to provide the second sensory stimulation that leads the user through the paced breathing exercise comprises causing the one or more sensory stimulators to provide a series of individual sensory stimuli that prompt the user to inhale, exhale, and pause, and iteratively extend an inspiratory time and an expiratory time of the user as tolerated by the user, for a duration of the paced breathing exercise.

In some embodiments, the system further comprises an electronic application executed by a computing device associated with the user. The electronic application is in communication with the controller, the one or more posture sensors, and/or the one or more sensory stimulators. The electronic application is configured to: provide visual prompts with the second sensory stimulation that lead the user through the paced breathing exercise; receive an indication from the user that the user is ready for the paced breathing exercise and communicate receipt of the indication to the controller; and/or facilitate review of stored information related to sleep of the user, respiration of the user, and/or the paced breathing exercise.

In some embodiments, the system further comprises a housing configured to house the one or more posture sensors, the one or more sensory stimulators, and the controller; and a belt coupled to the housing. The belt is configured to be worn by the user during the sleep session.

Another aspect of the present disclosure relates to a method for providing sleep positional therapy and paced breathing to a user for a sleep session with a therapy system. The system comprises one or more posture sensors, one or more sensory stimulators, and a controller. The method comprises generating, with the one or more posture sensors, output signals conveying information related to a posture of the user. The method comprises determining, with the controller, based on the output signals, whether the posture of the user has breached a posture threshold, and, responsive to a breach, causing the one or more sensory stimulators to provide first sensory stimulation to the user to prompt the user to change posture such that the posture of the user no longer breaches the posture threshold. The method comprises, responsive to determining that the posture of the user no longer breaches the posture threshold, causing, with the controller, the one or more sensory stimulators to provide second sensory stimulation that leads the user through a paced breathing exercise.

In some embodiments, the method comprises causing, with the controller, the one or more sensory stimulators to provide third sensory stimulation that prompts the user to indicate whether the user is ready for the paced breathing exercise before the user is led through the paced breathing exercise.

In some embodiments, the method comprises receiving, with the one or more posture sensors, an indication from the user that the user is ready for the paced breathing exercise, and causing, with the controller, the one or more sensory stimulators to provide the second sensory stimulation that leads the user through the paced breathing exercise responsive to the one or more posture sensors receiving the indication that the user is ready for the paced breathing exercise. [16] In some embodiments, the method comprises causing, with the controller, the one or more sensory stimulators to provide the second sensory stimulation that leads the user through the paced breathing exercise before or during the sleep session responsive to receiving the indication from the user that the user is ready for the paced breathing exercise, and independent of the determination of whether the posture of the user has breached the posture threshold.

In some embodiments, the system further comprises one or more physiological sensors, and the method further comprises generating, with the one or more physiological sensors, output signals conveying information related to respiration of the user, and causing, with the controller, delivery of the sensory stimulation during inhalation and exhalation portions of the paced breathing exercise based on the information in the output signals from the one or more physiological sensors.

In some embodiments, causing the one or more sensory stimulators to provide the second sensory stimulation that leads the user through the paced breathing exercise comprises causing the one or more sensory stimulators to provide a series of individual sensory stimuli that prompt the user to inhale, exhale, and pause, and iteratively extend an inspiratory time and an expiratory time of the user as tolerated by the user, for a duration of the paced breathing exercise.

In some embodiments, the system further comprises an electronic application executed by a computing device associated with the user. The electronic application is in communication with the controller, the one or more posture sensors, and/or the one or more sensory stimulators. In these embodiments, the method further comprises providing, with the electronic application, visual prompts with the second sensory stimulation that lead the user through the paced breathing exercise; receiving, with the electronic application, an indication from the user that the user is ready for the paced breathing exercise and communicating, with the electronic application, receipt of the indication to the controller; and/or facilitating, with the electronic application, review of stored information related to sleep of the user, respiration of the user, and/or the paced breathing exercise.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
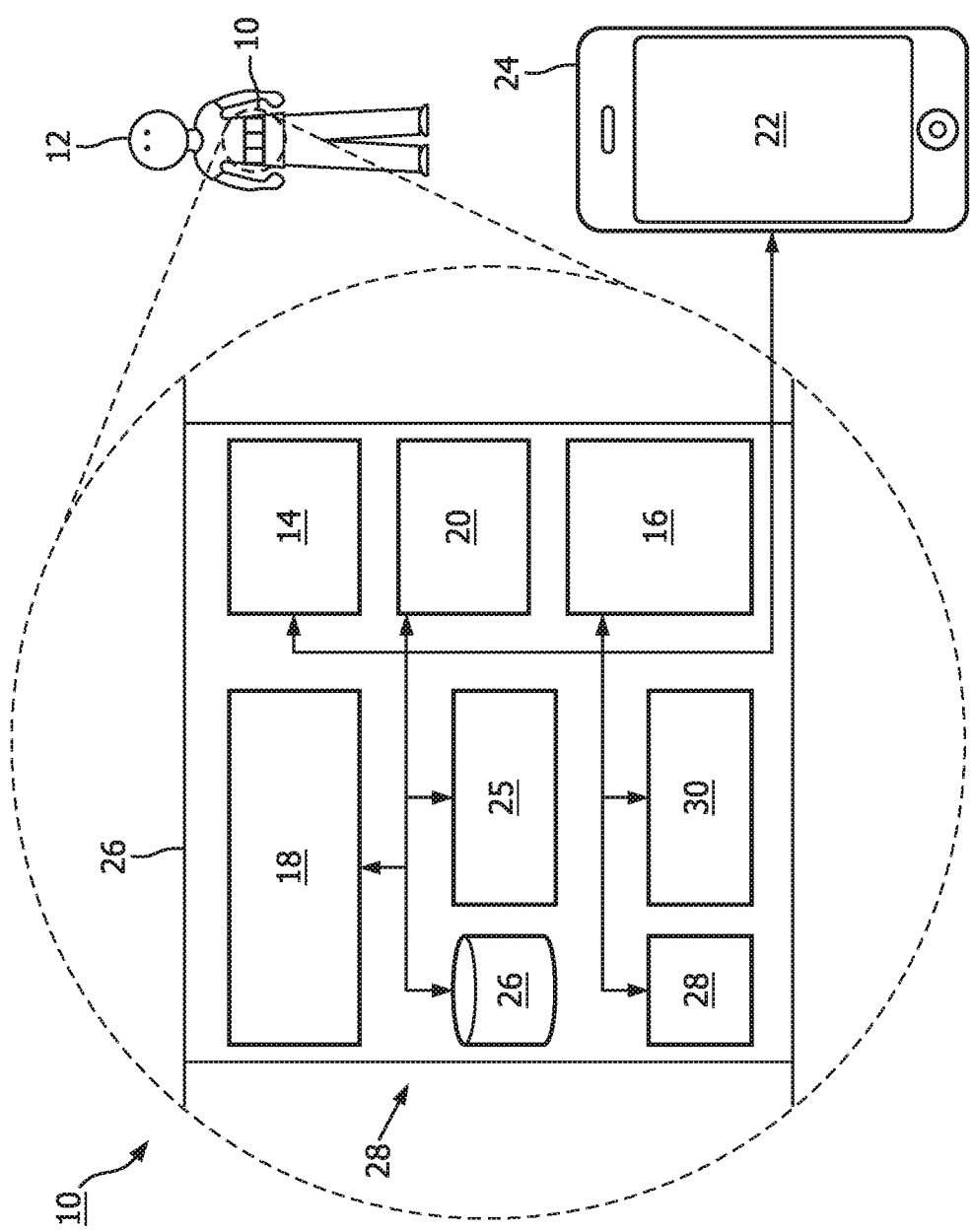
FIG. 1 is a schematic illustration of a system configured to provide sleep positional therapy and paced breathing to a user for a sleep session, in accordance with one or more embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to provide sleep positional therapy and paced breathing to a user 12 for a sleep session. In some embodiments, a sleep session may comprise any period of time when user 12 is sleeping and/or attempting to sleep. Sleep sessions may include nights of sleep, naps, and/or other sleeps sessions. Positional therapy (or sleep positional training) is an intervention for treating positional obstructive sleep apnea, positional snoring, assisting pregnant women (the American Pregnancy Association recommends "SOS"—"sleeping on side" and specifically on the left side), and/or other conditions in individuals. For some individuals, positional therapy is needed because the individuals fail to adhere to prescribed continuous positive airway pressure (CPAP) therapy regimes, and/or for other reasons. Individuals who suffer from positional obstructive sleep apnea (OSA) or positional snoring are more likely to suffer from anterior-posterior collapse of the soft palate region, from epiglottic closure, or from tongue base closure of the upper airway while lying in a supine position while sleeping, for example. Typically, for these individuals, airway collapse and subsequent sleep disordered breathing events (e.g., snoring, hypopneas, apneas, etc.) occur while sleeping in the supine position, and thus a therapy that encourages sleeping in any non-supine position (e.g., lateral or prone) may resolve the positional OSA and/or snoring.

Often, individuals who suffer from positional OSA or positional snoring do not adhere to prior developed therapies in the long-term. Electronic devices that have been developed to help improve adherence provide a stimulus to notify a user to move to a non-supine sleeping position, but then do not provide further assistance to the user to help the user fall back asleep. For example, vibrations from electronic sleep positional therapy devices tend to disrupt an individual's quality of sleep. Many of these individuals are so disrupted from sleep that they have difficulty falling back asleep again.

Diaphragmatic breathing, or paced breathing exercises, increase relaxation, decrease blood pressure, improve sympatho-vagal balance, and promote sleep. Diaphragmatic breathing exercises improve sleep onset latency and are safe. System 10 is configured to provide sleep positional therapy and paced breathing to user 12 for a sleep session. System 10 enhances initial sleep onset and/or a user's ability to fall back asleep after awakening by guiding user 12 in a paced breathing exercise. System 10 may guide user 12 through a paced breathing exercise when user 12 is initially trying to fall asleep, after prompting user 12 to change posture during a sleep session, and/or at other times. In some embodiments, system 10 includes one or more of a posture sensor 14, a physiological sensor 20, a sensory stimulator 16, a controller 18, an electronic application 22, a computing device 24, a user interface 25, electronic storage 26, a power supply 28, communications components 30, a housing 26, a belt 28, and/or other components.

Posture sensor 14 is configured to generate output signals conveying information related to a posture of user 12. The output signals are generated during a sleep session of user 12 and/or at other times. Posture may be, or be related to an overall body position of user 12, a position of one or more body parts of user 12, and/or other body position information. Posture sensor 14 may be and/or include an accelerometer, a gyroscope, an optical sensor (e.g., a video camera in the room), bed-based sensing (e.g., a pressure mat), a microphone array, radar, and/or other (on or off body) sensors. Posture sensor 14 is configured to generate output signals that convey information related to an acceleration, and orientation, an angular velocity, and/or other characteristics of user 12. Posture sensor 14 may generate output signals that convey information used to determine whether user 12 is in a supine or a non-supine position, whether user 12 is moving or has moved, whether user 12 is in a position that may cause sleep disordered breathing events, and/or other information, for example.

Physiological sensor 20 is configured to generate output signals conveying information related to respiration and/or other physiological characteristics of user 12. For example, physiological sensor 20 is configured to generate output signals conveying information related to breathing parameters such as a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, airflow parameters, and/or other breathing parameters of user 12. Physiological sensor 20 may comprise one or more sensors that measure such parameters directly (e.g., by sensing chest movements of user 12). Physiological sensor 20 may comprise one or more sensors that generate surrogate output signals related to the one or more breathing parameters indirectly. For example, physiological sensor 20 may comprise one or more sensors configured to generate an output based on a heart rate of user 12 (e.g., physiological sensor 20 may be or include a heart rate sensor such as a PPG), and/or other sensors. In some embodiments, sensor 20 may comprise one or more of a respiration sensor (e.g. a piezoelectric sensor, a polyvinylidene fluoride strain gauge, a respiratory inductance plethysmograph sensor, etc.), a pressure sensor, a vital signs sensor, an actigraphy sensor, electroencephalogram (EEG) electrodes, an electrooculogram (EOG) electrode, an electrocardiogram (EKG) electrode, a photoplethysmogram (PPG) sensor, a functional near infra-red sensor (fNIR), a temperature sensor, a microphone, and/or other sensors.

In some embodiments, the information in the output signals from physiological sensor 20 may be used to determine information related to posture of user 12, respiration of user 12, sleep of user 12, and/or other characteristics of user 12. For example, information in output signals from a heart rate sensor (e.g., a physiological sensor 20) may be used to determine a respiration pattern, a sleep stage, and/or other information about user 12. As another example, a posture sensor 14 such as an accelerometer may be used to determine the respiration pattern of user 12 based on chest movements of user 12 detected by the accelerometer, and/or the sleep stage of user 12 based on movement (or lack thereof) of user 12 during a sleep session (e.g., actigraphy).

As described above, in some embodiments, the information in the output signals from posture sensor 14 and/or physiological sensor 20 may indicate and/or be used to determine information about the sleep of user 12. The information in the output signals from posture sensor 14 and/or physiological sensor 20 may include information related to brain activity in user 12, cardiac activity in user 12, eye movement of user 12, and/or other physiological activity in user 12. For example, the information in the output signals from posture sensor 14 and/or physiological sensor 20 may be used to determine whether user 12 is asleep, the sleep stage of user 12, whether user 12 experiences arousals or microarousals, and/or other information. In some embodiments, the sleep stages of user 12 may be wakefulness, REM sleep, NREM Stage 1, 2, or 3 (e.g., N1, N2, N3), and/or other sleep stages.

In some embodiments, the information in the output signals from sensor 14 and/or 20 is used to control sensory stimulator 16 to provide sensory stimulation to user 12 (as described herein). Although sensors 14 and 20 are illustrated in FIG. 1 at a single location in system 10, this is not intended to be limiting. Sensors 14 and 20 may comprise sensors disposed in a plurality of locations, such as for example, at various locations coupled to user 12, within computing device 24, embedded in a mattress or pillow, on a night stand or side table, coupled to a wall or ceiling in a bedroom, and/or at other locations.

Sensory stimulator 16 is configured to provide sensory stimulation to user 12. Sensory stimulator 16 is configured to provide vibratory, auditory, visual, somatosensory, electric, magnetic, and/or other sensory stimulation to user 12 prior to a sleep session, during a sleep session, and/or at other times. For example, sensory stimulator 16 may be configured to provide stimuli to user 12 during a sleep session to provide sleep positional therapy with paced breathing to user 12. The vibratory, auditory, electric, magnetic, visual, somatosensory, and/or other sensory stimulation may include vibratory stimulation, auditory stimulation, visual stimulation, somatosensory stimulation, electrical stimulation, magnetic stimulation, a combination of different types of stimulation, and/or other stimulation. The vibratory, auditory, electric, magnetic, visual, somatosensory, and/or other sensory stimuli include vibrations, odors, sounds, visual stimulation, touches, tastes, somatosensory stimulation, haptic, electrical, magnetic, and/or other stimuli. The sensory stimulation may have an intensity, a timing, a duration, and/or other characteristics. For example, vibrations may be provided to user 12 to prompt user 12 to change posture, follow a paced breathing routine, and/or take other actions. The vibrations may include one or more series of vibrations of a determined length separated from each other by an inter-vibration interval. The intensity, length, timing, and/or other characteristics of individual vibrations may be modulated. Examples of sensory stimulator 16 may include one or more of a vibrator (e.g., with an oscillating transducer), a speaker, a coil generating a magnetic field, one or more light generators, a fragrance dispenser, and/or other devices. In some embodiments, sensory stimulator 16 is configured to adjust the type, intensity, timing, duration, and/or other parameters of the stimulation provided to user 12.

Controller 18 is configured to provide information processing capabilities in system 10. As such, controller 18 may comprise one or more of a digital processor, an analog processor, a digital circuit designed to process information, an analog circuit designed to process information, a state machine, and/or other mechanisms for electronically processing information. Although controller 18 is shown in FIG. 1 as a single entity, this is for illustrative purposes only. In some embodiments, controller 18 may comprise a plurality of processing units. These processing units may be physically located within the same device (e.g., within housing 26), or controller 18 may represent processing functionality of a plurality of devices operating in coordination. In some embodiments, a portion of controller 18 may be and/or be included in a computing device such as a desktop computer, a laptop computer, a smartphone, a tablet computer, a server, and/or other computing devices such as computing device 24 associated with user 12 and/or other people. Computing device 24 and/or other computing devices may run one or more electronic applications such as electronic application 22 having a graphical user interface configured to facilitate user interaction with system 10 (e.g., as described below).

Controller 18 is configured to determine whether or not the posture of user 12 breaches a posture threshold. Controller 18 is configured to make this posture threshold determination based on the output signals from posture sensor 14, and/or based on other information. In some embodiments, the posture threshold corresponds to a posture of user 12 that causes user 12 to experience sleep disordered breathing events such as snoring, apnea, and/or other sleep disordered breathing events. In some embodiments, the posture threshold corresponds to a supine position of user 12 and/or other body positions, for example. In some embodiments, criteria (e.g., thresholds on accelerometer data in the output signals from sensor 14) that define the posture threshold are programmed at the manufacture of system 10, adjustable by user 12 and/or other users via user interface 25, electronic application 22, computing device 24, and/or other components of system 10, and/or determined in other ways.

Controller 18 is configured to cause sensory stimulator 16 to provide sensory stimulation to user 12 that is configured to prompt user 12 to change posture. The sensory stimulation configured to prompt user 12 to change posture is provided responsive to a determination that the posture of user 12 breaches the posture threshold. The sensory stimulation configured to prompt user 12 to change posture is provided to prompt user 12 to change posture so the posture of user 12 no longer breaches the posture threshold. The sensory stimulation configured to prompt user 12 to change posture may be, for example, vibrations, auditory stimulation (e.g., tones, music, etc.), and/or other stimulation.

Figure 2A:
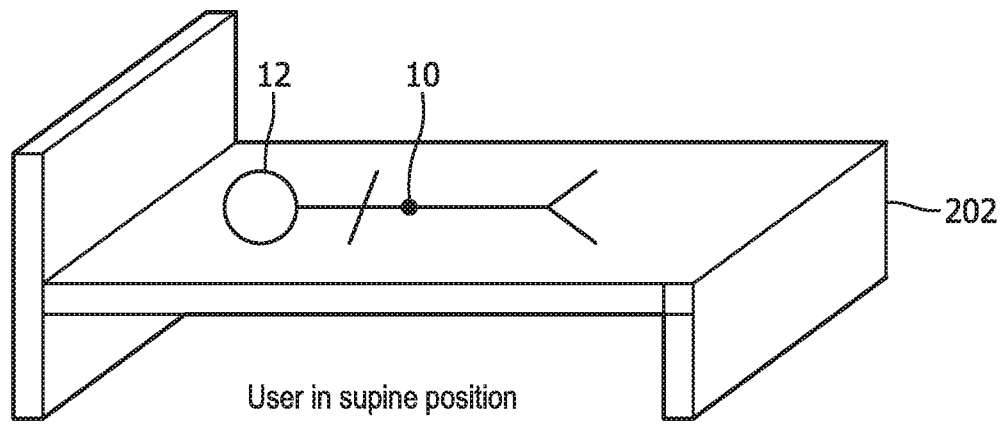
FIG. 2A and FIG. 2B illustrate the user changing posture during a sleep session, in accordance with one or more embodiments.
Figure 2B:
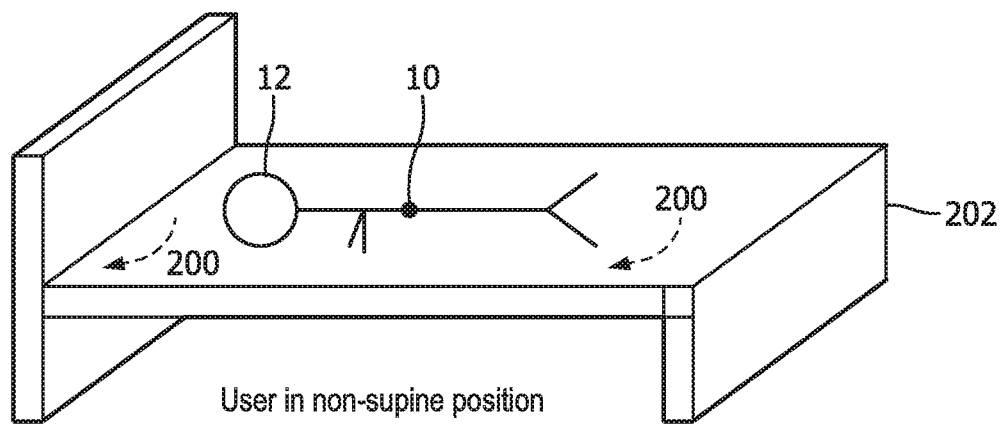

By way of a non-limiting example, FIG. 2A and FIG. 2B illustrate user 12 changing posture 200 during a sleep session. As shown in FIG. 2A, user 12 is in a supine position in bed 202. Controller 18 (FIG. 1) of system 10 is configured to cause sensory stimulator 16 (FIG. 1) to provide sensory stimulation to user 12 that is configured to prompt user 12 to change posture. As shown in FIG. 2B, user 12 rolls from the supine position shown in FIG. 2A to a non-supine position. The sensory stimulation configured to prompt user 12 to change posture is provided responsive to a determination that the posture of user 12 breaches the posture threshold (e.g., indicating that user 12 is in the supine position shown in FIG. 2A). The sensory stimulation configured to prompt user 12 to change posture is provided to prompt user 12 to change posture so the posture of user 12 no longer breaches the posture threshold (e.g., such that user 12 rolls to the non-supine position shown in FIG. 2B). The sensory stimulation configured to prompt user 12 to change posture may be, for example, vibrations, auditory stimulation (e.g., tones, music, etc.), and/or other stimulation.

Returning to FIG., 1, controller 18 is configured to cause sensory stimulator 18 to provide sensory stimulation to user 12 that leads user 12 through a paced breathing exercise. The sensory stimulation that leads user 12 through the paced breathing exercise is provided responsive to a determination that the posture of user 12 no longer breaches the posture threshold (e.g., responsive to user 12 changing posture after being prompted as described above). In some embodiments, controller 18 is configured to determine, based on the information in the output signals from posture sensor 14, physiological sensor 20, and/or other information, that user 12 is awake and may benefit from a diaphragmatic breathing exercise. In some embodiments, controller 18 is configured to cause sensory stimulator 16 to deliver the sensory stimulation that leads user 12 through the paced breathing exercise responsive to the determination that the posture of user 12 no longer breaches the posture threshold, the determination that user 12 is awake and may benefit from a diaphragmatic breathing exercise, and/or other information.

In some embodiments, controller 18 is configured to determine a relative agitation state of user 12. The relative agitation state of user 12 may be determined based on an agitation spectrum that ranges from relaxed to agitated. The agitation state may be determined based on breathing pattern and/or heart rate information determined based on the information in the output signals from posture sensor 14 and/or physiological sensor 20, and/or other information. Controller 18 is configured to determine whether to cause sensory stimulator 16 to lead user 12 through a paced breathing exercise based on the relative agitation state of user 12.

Controller 18 may be configured to cause sensory stimulator 16 to lead user 12 through a paced breathing exercise responsive to a determination that user 12 is relatively agitated, for example. In some embodiments, controller 18 determines the length of the paced breathing exercise based on the relative agitation of user 12. For example, a paced breathing exercise for a relatively agitated user may be longer than a paced breathing exercise for a more relaxed user 12.

In some embodiments, agitation (or an indication of agitation) may be determined based on the (e.g., physiological) information in the output signals from posture sensor(s) 14, physiological sensor(s) 20, and/or other information. For example, agitation may be determined using actigraphy (e.g. an accelerometer, or other likely body position determination means), windowed over a 20 second period (for example), to determine that user 12 is more active and more restless than expected while attempting to fall asleep. As another example, heart rate variability may be used to determine agitation (or an indication of agitation), based on when user 12 has high sympathetic activation (i.e. increased low-frequency power) and low parasympathetic activation, relative to expectations, or a baseline for user 12. As another example, agitation (or an indication of agitation) may be determined using an EEG signal (e.g. increased beta wave activity) to detect anxious rumination.

In some embodiments, the sensory stimulation that leads user 12 through the paced breathing exercise is the same as or different from the sensory stimulation configured to prompt user 12 to change posture. For example, the sensory stimulation that leads user 12 through the paced breathing exercise and the sensory stimulation configured to prompt user 12 to change posture may both be vibrations. As another example, the sensory stimulation that leads user 12 through the paced breathing exercise may be auditory tones, and the sensory stimulation configured to prompt user 12 to change posture may be vibrations, or vice versa. In some embodiments, the sensory stimulation that leads user 12 through the paced breathing exercise and the sensory stimulation configured to prompt user 12 to change posture may both be vibrations (or tones, or other sensory stimulation), but have different durations, frequencies, intervals, and/or other characteristics that distinguish the sensory stimulation that leads user 12 through the paced breathing exercise from the sensory stimulation configured to prompt user 12 to change posture.

In some embodiments, the sensory stimulation that leads user 12 through the paced breathing exercise and the sensory stimulation configured to prompt user 12 to change posture may be programmed at the manufacture of system 10, may be adjustable by user 12 and/or other users, and/or may be determined in other ways. For example, in some embodiments, the sensory stimulation that leads user 12 through the paced breathing exercise and/or the sensory stimulation configured to prompt user 12 to change posture may be user customizable by type (e.g., haptic, audio, or other types), intensity (e.g. mild, medium, strong), frequency (e.g. accelerating vibrations during inhale and decelerating vibrations during exhale), and/or other adjustable characteristics. These adjustments may be facilitated by controller 18 via user interface 25, electronic application 22, and/or other components of system 10, for example.

In some embodiments, the paced breathing exercise is configured to help user 12 fall asleep. In some embodiments, controller 18 is configured such that the paced breathing exercise ends after a pre-determined amount of time elapses after the start of the paced breathing exercise. In some embodiments, controller 18 is configured such that the paced breathing exercise ends responsive to controller 18 detecting that user 12 has fallen asleep. Controller 18 may determine that user 12 has fallen asleep based on the information in the output signals from sensors 14 and 20 and/or other information, for example.

In some embodiments, controller 18 causes sensory stimulator 16 to provide sensory stimulation to user 12 that prompts user 12 to indicate whether user 12 is ready for the paced breathing exercise before user 12 is led through the paced breathing exercise. In some embodiments, controller 18 is configured to receive, via posture sensor 14, an indication from user 12 that user 12 is ready for the paced breathing exercise, and cause sensory stimulator 16 to provide the sensory stimulation that leads user 12 through the paced breathing exercise responsive to posture sensor 14 receiving the indication that user 12 is ready for the paced breathing exercise.

By way of a non-limiting example, controller 18 may cause sensory stimulator 16 to provide a haptic prompt (e.g. two short vibrations) to user 12, which, if user 12 acknowledges within a predetermined amount of time (e.g., 10 seconds) by, for example, double-tapping housing 26 (e.g., which is detected by an accelerometer based posture sensor 14), controller 18 causes sensory stimulator 16 to commence a session of diaphragmatic breathing, synchronized with the breathing pattern of user 12. Controller 18 may cause sensory stimulator 16 to provide haptic feedback to inform user 12 to inhale and exhale (e.g. increasing frequency taps during inhalation, pause during exhalation), extending the inspiratory and expiratory time as tolerated by user 12 (toward a predetermined target of, e.g., six breaths per minute) for the duration of the session.

For example, system 10 may measure user 12's typical inhalation and exhalation times and determine a target inhalation and exhalation time (e.g., either automatically or based on a setting). From the current inhalation and exhalation times, the target inhalation and exhalation times, and the expected time of the paced breathing session, system 10 may target an inhalation and exhalation time for each breath (e.g. a breath time schedule). System 10 may then initiate a paced breath session starting at the next detected start of inhalation, providing 'taps' of increasing frequency over time during inhalation, until end inhalation. For example, the starting frequency of taps may be 2 taps/sec and the ending frequency may be 20 taps/sec (these examples are not intended to be limiting). The taps may or may not pause at the end of inhalation in order to denote an end-inspiratory pause. During exhalation, system 10 may either reverse the direction of frequency of taps (decreasing frequency over time, until there are no taps by end-exhalation), or have no taps (i.e. quiet during exhalation). The next breath may be initiated by a similar sequence of taps, either slightly extending the inspiratory and expiratory times if user 12 was determined to have breathed in synchrony with (or with a longer breath period than) the haptic prompting or keeping the same breath time if the user was desynchronous with the breathing prompt of the prior breath or if the target breath period was achieved.

As another example, sensory stimulator 16 may be controlled to vibrate in a pattern of 2-4 seconds and 4-6 seconds to alert user 12 to breathe in on the shorter 2-4 second vibration and exhale on the longer 4-6 second vibration. This vibration pattern may occur 6-8 times over a 1 minute period with the entire session of paced breathing lasting five minutes.

Controller 18 may be configured such that the session is terminated when either a predetermined session duration is exceeded, or if the user falls asleep (determined based on the output signals from posture sensor 14 and/or physiological sensor 20—e.g., by actigraphy or by desynchronization with the breathing exercise). The example durations and quantities cited above are not intended to be limiting.

In some embodiments, the paced breathing exercise may be open loop or closed loop controlled by controller 18, and automatic, or user 12 initiated. Open loop control may include providing the paced breathing exercise independent of the information about the respiration of user 12 from physiological sensor 20 and/or posture sensor 14. Closed loop control may include providing the paced breathing exercise based on the information about the respiration of user 12 from physiological sensor 20 and/or posture sensor 14, and corresponding to the respiration of user 12.

For example, in some embodiments, causing sensory stimulator 16 to provide the sensory stimulation that leads user 12 through the paced breathing exercise comprises causing sensory stimulator 16 to provide a series of individual sensory stimuli that prompt user 12 to inhale, exhale, and pause, and iteratively extend an inspiratory time and an expiratory time of user 12 as tolerated by user 12, for a duration of the paced breathing exercise. In some embodiments, controller 18 is configured to cause delivery of this sensory stimulation during inhalation and exhalation portions of the paced breathing exercise based on the information in the output signals from the physiological sensor 20 (and/or the information in the output signals from posture sensor 14 when posture sensor 14 is an accelerometer and the information in the output signals is used to determine the breathing pattern of user 12). As another example, in some embodiments, the sensory stimulation that leads user 12 through the paced breathing exercise is provided to user 12 before or during the sleep session responsive to controller 18 receiving (e.g., via posture sensor 14) the indication from user 12 that user 12 is ready for the paced breathing exercise, and independent of the determination of whether the posture of user 12 has breached the posture threshold. Controller 18 may be configured such that, in such embodiments, user 12 may actuate the paced breathing exercise by tapping system 10 (e.g., housing 26) twice (for example) within a predetermined amount of time (e.g., the first ten minutes) of device power up, for example.

Electronic Application 22 is executed by computing device 24 associated with user 12. Electronic application 22 (along with controller 18 and/or other components of system 10) is configured such that user 12 can also actuate the paced breathing exercise through electronic application 22 (e.g., via computing device 24 or another wireless viewer). In some embodiments, electronic application 22 is configured to provide visual prompts coordinated with the sensory stimulation that lead user 12 through the paced breathing exercise (e.g., an expanding and contracting balloon, a waveform that moves up and down, etc.). In some embodiments, electronic application 22 is configured to receive an indication from user 12 that user 12 is ready for the paced breathing exercise and communicate receipt of the indication to controller 18.

In some embodiments, electronic application 22 is configured to facilitate review of stored information related to sleep of the user, respiration of the user, and/or the paced breathing exercise. In these embodiments, controller 18 may be configured to monitor and generate (e.g., based on the information in the output signals from sensor 14, sensor 20, and/or other information) user information related to usage and efficacy of the paced breathing session (e.g., determining and/or recording a number of paced breathing sessions utilized, a length of time to fall asleep after paced breathing session commences, and/or other information based on the output signals). In these embodiments, controller 18 may generate user information related to sleep such as sleep and wakeup times, sleep stages, sleep efficiency, sleep disturbances, etc. In these embodiments, controller 18 may be configured to generate longitudinal (diary) data that may be recalled (e.g., from electronic storage 26) and reviewed (e.g., using electronic application 22) by user 12 and/or others. In these embodiments, electronic application 22 and/or controller 18 may be configured such that the user information related to usage and efficacy and/or other user information may be wirelessly transferrable to or from a computing device such as computing device 24 and/or other computing devices.

Computing device 24 may be associated with user 12 and/or other people. Computing device 24 may be a desktop computer, a laptop computer, a smart phone, a tablet, or any other networked computing device having a display, a user input device (e.g., buttons, keys, voice recognition, or a single or multi-touch touchscreen), memory (such as a tangible, machine-readable, non-transitory memory), a network interface, a portable energy source (e.g., a battery), and a processor coupled to each of these components. The memory of mobile computing device 24 may store instructions that when executed by the associated processor provide an operating system and various applications, including electronic application 22. In some embodiments, electronic application 22 is operative to provide a graphical user interface that communicates with other components of system 10 (e.g., communication components 30, controller 18, etc.) and facilitates user interaction with system 10.

User interface 25 is configured to provide an interface between system 10 and user 12, and/or other users through which user 12 and/or other users may provide information to and receive information from system 10. This enables data, cues, results, and/or instructions and any other communicable items, collectively referred to as "information," to be communicated between a user (e.g., user 12) and one or more of sensor 14, sensor 20, sensory stimulator 16, controller 18, electronic application 22, computing device 24, electronic storage 26, power supply 28, communications components 30, and/or other components of system 10. In some embodiments, some or all of user interface 25 may be and/or be included in a computing device such as computing device 24 (e.g., a desktop computer, a laptop computer, a smartphone, a tablet computer, and/or other computing devices.

Examples of interface devices suitable for inclusion in user interface 25 comprise a keypad, buttons, switches, a keyboard, knobs, levers, a display screen, a touch screen, speakers, a microphone, an indicator light, an audible alarm, a printer, a tactile feedback device (e.g., including a motion sensor (passive infrared or microwave) that reacts to hand waves), and/or other interface devices. In some embodiments, user interface 25 comprises a plurality of separate interfaces. In some embodiments, user interface 25 comprises at least one interface that is provided integrally with housing 26 and/or other components of system 10. In some embodiments, user interface 25 is configured to communicate wirelessly with communications components 30, controller 18, and/or other components of system 10.

It is to be understood that other communication techniques, either hard-wired or wireless, are also contemplated by the present disclosure as user interface 25. For example, the present disclosure contemplates that user interface 25 may be integrated with a removable storage interface provided by electronic storage 26. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 25 comprise, but are not limited to, an RS-232 port, RF link, an IR link, modem (telephone, cable or other). In short, any technique for communicating information with system 10 is contemplated by the present disclosure as user interface 25.

Electronic storage 26 comprises electronic storage media that electronically stores information. The electronic storage media of electronic storage 26 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 26 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 26 may store software algorithms, information determined by controller 18, information received via user interface 25 and/or sensors 14 and 20, and/or other information that enables system 10 to function as described herein. Electronic storage 26 may be (in whole or in part) a separate component within system 10, or electronic storage 26 may be provided (in whole or in part) integrally with one or more other components of system 10 (e.g., within housing 26).

Power supply 28 is configured to power posture sensor 14, physiological sensor 20, sensory stimulator 16, controller 18, user interface 25, electronic storage 26, communications components 30, and/or other components of system 10 in a portable manner. Power supply 28 may comprise one or more power sources connected in series and/or in parallel. In some embodiments, power supply 28 is rechargeable. Power supply 28 may be recharged via a home AC power source, a car battery outlet, an airplane power outlet, a USB port, a non-contact charging circuit, and/or other recharging methods. Examples of portable power sources that may be included as power supply 28 include one or more DC batteries, Lithium Ion and/or Lithium Polymer Cells, Nickel Metal Hydride, and/or other portable power sources.

Communications components 30 comprise components that facilitate communication of information via a network (e.g., the internet), equipment related to Wi-Fi technology, equipment related to Bluetooth® technology, scanners, input/output interfaces, and/or other resources. Communication components 30 may be configured to communicate with electronic application 22, computing device 24, and/or other components of system 10 via wired and/or wireless connections, via a network (e.g., a local area network and/or the internet), via cellular technology, via Wi-Fi technology, and/or via other resources. In some embodiments, communication components 30 may be configured to communicate via a text message, an email, a phone call, an electronic app and/or web page (e.g., electronic application 22, a web page displayed by computing device 24, etc.), an electronic app notification, and/or with other communications.

Housing 26 is configured to contain or otherwise house posture sensor 14, physiological sensor 20, sensory stimulator 16, controller 18, user interface 25, electronic storage 26, power supply 28, communications components 30, and/or other components of system 10. Housing 26 is configured to contain the components of system 10 in a space small enough to be comfortably worn by user 12 during a sleep session. In FIG. 1, posture sensor 14, physiological sensor 20, sensory stimulator 16, controller 18, user interface 25, electronic storage 26, power supply 28, communications components 30, and/or other components of system 10 are shown housed by housing 26 and forming a single entity. This is not intended to be limiting. Some and/or all of the components of system 10 and/or other components may form one or more separate devices. For example, posture sensor 14 may be a separate device pointed at (e.g., a camera) user 12, a sensor coupled to a mattress on which user 12 sleeps, and/or other sensors not housed by housing 26. As another example, physiological sensor 20 may be worn by and/or otherwise coupled to user 12 separately from housing 26. As still another example, sensory stimulator 16 may be or include speakers configured to direct auditory stimulation toward user 12. The speakers may be placed in the environment where user 12 sleeps, separate from housing 26, for example. These devices may be configured to communicate wireless and/or via wires with other components of system 10 and/or other devices.

Belt 28 is configured to be coupled to housing 26. In some embodiments, belt 28 may be removably coupled to housing 26. For example, belt 28 may be removably coupled to housing 26 by way of a pocket in belt 28 configured to hold housing 26, straps, hooks, clips, clamps, and/or other components of belt 28 configured to removably couple with housing 26. In some embodiments, belt 28 may be fixedly coupled to housing 26. For example, housing 26 may sewn into or onto belt 28, and/or housing 26 may be fixedly coupled to belt 28 by other methods. Belt 28 is configured to be worn by user 12 during the sleep session. Belt 28 may be worn by user 12 around the chest, waist, or other body parts of user 12. Belt 28 may be formed by a strap or other strip of material configured to wrap around the chest, waist, or other body parts of user 12. Belt 28 may be formed from a soft and/or flexible material configured to enhance the comfort of user 12 during a sleep session and/or other materials.

Figure 3:
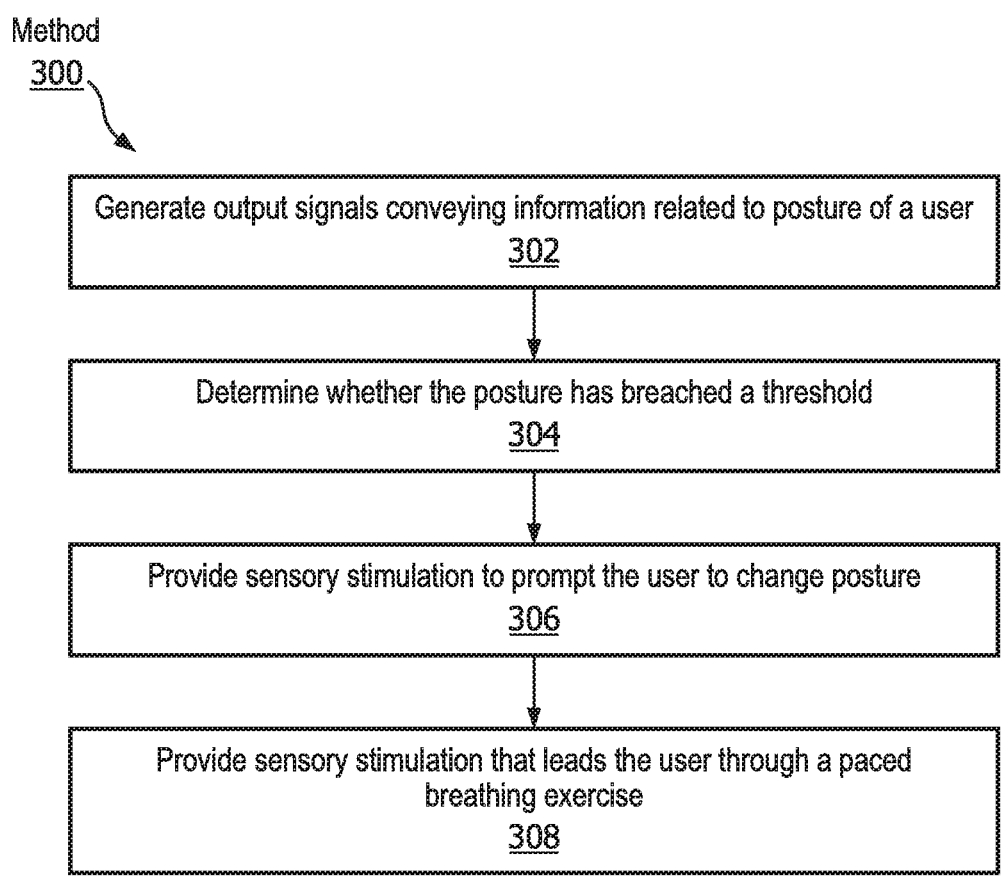
FIG. 3 illustrates a method for providing sleep positional therapy and paced breathing to a user for a sleep session with a therapy system, in accordance with one or more embodiments.

FIG. 3 illustrates method 300 for providing sleep positional therapy and paced breathing to a user for a sleep session with a therapy system. The system comprises one or more posture sensors, one or more physiological sensors, one or more sensory stimulators, one or more controllers, and/or other components. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices such as one or more controllers 18 described herein (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/ or software to be specifically designed for execution of one or more of the operations of method 300.

At an operation 302, output signals conveying information related to the posture of a user are generated. The output signals are generated during a sleep session of the user and/or at other times. In some embodiments, operation 302 is performed by sensors the same as or similar to posture sensors 14 (shown in FIG. 1 and described herein).

At an operation 304, a determination of whether or not the posture of the user breaches a posture threshold is made. In some embodiments, the posture threshold indicates whether the user is in a supine position. The posture determination is made based on the information in the output signals from the posture sensors and/or based on other information. In some embodiments, operation 304 is performed by a controller the same as or similar to controller 18 (shown in FIG. 1 and described herein).

At an operation 306, sensory stimulation configured to prompt the user to change posture is provided to the user. The sensory stimulation configured to prompt the user to change posture is provided responsive to a determination that the posture of the user breaches the posture threshold. The sensory stimulation configured to prompt the user to change posture is provided to prompt the user to change posture so the posture of the user no longer breaches the posture threshold. In some embodiments, operation 308 is performed by a sensory stimulator the same as or similar to sensory stimulator 16 (shown in FIG. 1 and described herein).

At an operation 308, sensory stimulation that leads the user through a paced breathing exercise is provided to the user. The sensory stimulation that leads the user through the paced breathing exercise is provided responsive to a determination that the posture of the user no longer breaches the posture threshold. In some embodiments, the paced breathing exercise is configured to help the user fall asleep.

In some embodiments, operation 308 comprises providing sensory stimulation to the user that prompts the user to indicate whether the user is ready for the paced breathing exercise before the user is led through the paced breathing exercise. In some embodiments, operation 308 comprises receiving, with the one or more posture sensors, an indication from the user that the user is ready for the paced breathing exercise, and causing, with the controller, the one or more sensory stimulators to provide the second sensory stimulation that leads the user through the paced breathing exercise responsive to the one or more posture sensors receiving the indication that the user is ready for the paced breathing exercise. In some embodiments, the sensory stimulation that leads the user through the paced breathing exercise is provided to the user before or during the sleep session responsive to receiving the indication from the user that the user is ready for the paced breathing exercise, and independent of the determination of whether the posture of the user has breached the posture threshold. In some embodiments, causing the one or more sensory stimulators to provide the second sensory stimulation that leads the user through the paced breathing exercise comprises causing the one or more sensory stimulators to provide a series of individual sensory stimuli that prompt the user to inhale, exhale, and pause, and iteratively extend an inspiratory time and an expiratory time of the user as tolerated by the user, for a duration of the paced breathing exercise. In some embodiments, operation 308 is performed by a posture sensor, a controller, and/or a sensory stimulator the same as or similar to posture sensor 14, controller 18, and/or sensory stimulator 16 (shown in FIG. 1 and described herein).

In some embodiments, method 300 comprises generating, with the one or more physiological sensors, output signals conveying information related to respiration of the user, and causing, with the controller, delivery of the sensory stimulation during inhalation and exhalation portions of the paced breathing exercise based on the information in the output signals from the one or more physiological sensors.

In some embodiments, the system further comprises an electronic application executed by a computing device associated with the user. In such embodiments, the method further comprises: providing, with the electronic application, visual prompts with the second sensory stimulation that lead the user through the paced breathing exercise; receiving, with the electronic application, an indication from the user that the user is ready for the paced breathing exercise and communicating, with the electronic application, receipt of the indication to the controller; and/or facilitating, with the electronic application, review of stored information related to sleep of the user, respiration of the user, and/or the paced breathing exercise.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to provide sleep positional therapy and paced breathing to a user for a sleep session, the system comprising:
   one or more posture sensors configured to generate output signals conveying information related to whether the user is lying down in a supine position or lying down in a non-supine lateral or prone position;
   one or more sensory stimulators configured to provide sensory stimulation to the user; and
   a controller coupled to the one or more posture sensors and the one or more sensory stimulators, the controller configured to:
      determine, based on the output signals, whether the user is lying down in the supine position, and, responsive to determining that the user is lying down in the supine position, cause the one or more sensory stimulators to provide first sensory stimulation to the user to prompt the user to change posture such that the user is lying down in the non-supine lateral or prone position; and responsive to determining that the user is lying down in the non-supine lateral or prone position, cause the one or more sensory stimulators to provide second sensory stimulation that leads the user through a paced breathing exercise configured to help the user fall asleep during the sleep session while lying down in the non-supine lateral or prone position.

2. The system of claim 1, wherein the controller is further configured to cause the one or more sensory stimulators to provide third sensory stimulation that prompts the user to indicate whether the user is ready for the paced breathing exercise before the user is led through the paced breathing exercise.

3. The system of claim 1, wherein the one or more posture sensors are further configured to receive an indication from the user that the user is ready for the paced breathing exercise, and the controller is further configured to cause the one or more sensory stimulators to provide the second sensory stimulation that leads the user through the paced breathing exercise responsive to the one or more posture sensors receiving the indication that the user is ready for the paced breathing exercise.

4. The system of claim 1, further comprising one or more physiological sensors configured to generate output signals conveying information related to respiration of the user, wherein the controller is configured to cause delivery of the sensory stimulation during inhalation and exhalation portions of the paced breathing exercise based on the information in the output signals from the one or more physiological sensors.

5. A system configured to provide sleep positional therapy and paced breathing to a user for a sleep session, the system comprising:
one or more posture sensors configured to generate output signals conveying information related to a posture of the user;
one or more sensory stimulators configured to provide sensory stimulation to the user; and
a controller coupled to the one or more posture sensors and the one or more sensory stimulators, the controller configured to:
determine, based on the output signals, whether the posture of the user has breached a posture threshold, and, responsive to a breach, cause the one or more sensory stimulators to provide first sensory stimulation to the user to prompt the user to change posture such that the posture of the user no longer breaches the posture threshold; and
responsive to determining that the posture of the user no longer breaches the posture threshold, cause the one or more sensory stimulators to provide second sensory stimulation that leads the user through a paced breathing exercise configured to help the user fall asleep during the sleep session, wherein the controller is configured such that causing the one or more sensory stimulators to provide the second sensory stimulation that leads the user through the paced breathing exercise comprises causing the one or more sensory stimulators to provide a series of individual sensory stimuli that prompt the user to inhale, exhale, and pause, and iteratively extend a length of an inspiratory time and iteratively extend a length of an expiratory time of the user for a duration of the paced breathing exercise.

6. The system of claim 1, further comprising an electronic application executed by a computing device associated with the user, the electronic application in communication with the controller, the one or more posture sensors, and/or the one or more sensory stimulators, the electronic application configured to: provide visual prompts with the second sensory stimulation that lead the user through the paced breathing exercise; receive an indication from the user that the user is ready for the paced breathing exercise and communicate receipt of the indication to the controller; and/or
facilitate review of stored information related to sleep of the user, respiration of the user, and/or the paced breathing exercise.

7. The system of claim 1, further comprising a housing configured to house the one or more posture sensors, the one or more sensory stimulators, and the controller; and a belt coupled to the housing, the belt configured to be worn by the user during the sleep session.

8. A method for providing sleep positional therapy and paced breathing to a user for a sleep session with a therapy system, the system comprising one or more posture sensors, one or more sensory stimulators, and a controller, the method comprising:
generating, with the one or more posture sensors, output signals conveying information related to whether the user is lying down in a supine position or lying down in a non-supine lateral or prone position;
determining, with the controller, based on the output signals, whether the user is lying down in the supine position, and, responsive to determining that the user is lying down in the supine position, causing the one or more sensory stimulators to provide first sensory stimulation to the user to prompt the user to change posture such that the user is lying down in the non-supine lateral or prone position; and
responsive to determining that the user is lying down in the non-supine lateral or prone position, causing, with the controller, the one or more sensory stimulators to provide second sensory stimulation that leads the user through a paced breathing exercise configured to help the user fall asleep during the sleep session while lying down in the non-supine lateral or prone position.

9. The method of claim 8, further comprising causing, with the controller, the one or more sensory stimulators to provide third sensory stimulation that prompts the user to indicate whether the user is ready for the paced breathing exercise before the user is led through the paced breathing exercise.

10. The method of claim 8, further comprising receiving, with the one or more posture sensors, an indication from the user that the user is ready for the paced breathing exercise, and causing, with the controller, the one or more sensory stimulators to provide the second sensory stimulation that leads the user through the paced breathing exercise responsive to the one or more posture sensors receiving the indication that the user is ready for the paced breathing exercise.

11. The method of claim 8, wherein the system further comprises one or more physiological sensors, the method further comprising generating, with the one or more physiological sensors, output signals conveying information related to respiration of the user, and causing, with the controller, delivery of the sensory stimulation during inhalation and exhalation portions of the paced breathing exercise based on the information in the output signals from the one or more physiological sensors.

12. A method for providing sleep positional therapy and paced breathing to a user for a sleep session with a therapy system, the system comprising one or more posture sensors, one or more sensory stimulators, and a controller, the method comprising:

generating, with the one or more posture sensors, output signals conveying information related to a posture of the user;

determining, with the controller, based on the output signals, whether the posture of the user has breached a posture threshold, and, responsive to a breach, causing the one or more sensory stimulators to provide first sensory stimulation to the user to prompt the user to change posture such that the posture of the user no longer breaches the posture threshold; and responsive to determining that the posture of the user no longer breaches the posture threshold, causing, with the controller, the one or more sensory stimulators to provide second sensory stimulation that leads the user through a paced breathing exercise configured to help the user fall asleep during the sleep session, wherein causing the one or more sensory stimulators to provide the second sensory stimulation that leads the user through the paced breathing exercise comprises causing the one or more sensory stimulators to provide a series of individual sensory stimuli that prompt the user to inhale, exhale, and pause, and iteratively extend a length of an inspiratory time and iteratively extend a length of an expiratory time of the user for a duration of the paced breathing exercise.

13. The method of claim 8, wherein the system further comprises an electronic application executed by a computing device associated with the user, the electronic application in communication with the controller, the one or more posture sensors, and/or the one or more sensory stimulators, the method further comprising: providing, with the electronic application, visual prompts with the second sensory stimulation that lead the user through the paced breathing exercise; receiving, with the electronic application, an indication from the user that the user is ready for the paced breathing exercise and communicating, with the electronic application, receipt of the indication to the controller; and/or facilitating, with the electronic application, review of stored information related to sleep of the user, respiration of the user, and/or the paced breathing exercise.

* * * * *